United States Patent
Gough et al.

(10) Patent No.: US 9,506,106 B2
(45) Date of Patent: Nov. 29, 2016

(54) WEIGHT SENSOR SUITABLE FOR USE UNDER A BED WITH A DEFORMABLE PLATE MOUNTED TO A BASE AT THREE CONTACT POINTS

(71) Applicant: Genetrainer Limited, Berkshire (GB)

(72) Inventors: Julian Gough, Avon (GB); Alexander Kalogroulis, Surrey (GB); Ralph Pethica, Oxfordshire (GB); Patrick Dura, Asnieres sur Seine (FR)

(73) Assignee: Genetrainer Limited, Berkshire (GB)

( * ) Notice: Subject to any disclaimer, the term of this patent is extended or adjusted under 35 U.S.C. 154(b) by 0 days.

(21) Appl. No.: 14/513,248

(22) Filed: Oct. 14, 2014

(65) Prior Publication Data
US 2015/0101870 A1   Apr. 16, 2015

(30) Foreign Application Priority Data
Oct. 15, 2013   (GB) .................................. 1318201.9

(51) Int. Cl.
*G01G 3/14* (2006.01)
*G01G 19/44* (2006.01)
(Continued)

(52) U.S. Cl.
CPC ............... *C12Q 1/6806* (2013.01); *C12Q 1/68* (2013.01); *C12Q 1/6816* (2013.01); *C12Q 1/6841* (2013.01); *G01N 33/5011* (2013.01); *G01N 33/582* (2013.01)

(58) Field of Classification Search
CPC .. G01G 3/141; G01G 3/1402; G01G 19/445; G01G 21/23; G01G 23/3735; G01G 3/08; A61B 5/1115; A61B 2562/046; A61G 7/05; A61G 2007/0527; A61G 2203/44; G01L 1/2206; G01L 1/044
See application file for complete search history.

(56) References Cited

U.S. PATENT DOCUMENTS 3,266,584 A * 8/1966 Lee .................. G01G 3/1404
                                                    177/134
3,722,611 A * 3/1973 Tirkkonen ............... A61G 7/00
                                                    177/144
(Continued)

FOREIGN PATENT DOCUMENTS

CA     2 290 185 A1    5/2000
CA     2 590 185 A1    5/2007
(Continued)

OTHER PUBLICATIONS

Extended European Search Report, EP App. 14275218.7, Apr. 9, 2015 (7 pages).
(Continued)

*Primary Examiner* — Randy W Gibson
(74) *Attorney, Agent, or Firm* — Sutherland Asbill & Brennan LLP (57) ABSTRACT

A weight sensor may include a weighing platform and a load cell coupled to the platform to sense a weight applied to the platform. The load cell may include a deformable plate with one or more strain gauges arranged to provide an electrical signal representing the weight applied to the platform, and a base supporting the load cell, wherein the deformable plate is movably mounted to the base at only three contact points, the contact points allowing lateral movement of the plate relative to the base when the plate deforms in response to a weight applied to the platform. The weight sensor makes it possible to independently monitor the weight and weight shifting of two people sharing the same bed. The weight sensor is self-centering when a load is applied off-center to the platform, which is particularly beneficial when such a weight sensor is used underneath a bed, e.g., under a bed leg or other support member which may not be aligned centrally over the weight sensor. Beneficially the sensor is not unduly affected by minor misalignment of the leg of a bed relative to the load cell.

21 Claims, 11 Drawing Sheets

(51) Int. Cl.
  *G01G 21/23*  (2006.01)
  *A61G 7/05*  (2006.01)
  *C12Q 1/68*  (2006.01)
  *G01N 33/50*  (2006.01)
  *G01N 33/58*  (2006.01)

(56) References Cited

U.S. PATENT DOCUMENTS

| | | | | |
|---|---|---|---|---|
| 4,002,215 A | * | 1/1977 | Harvill | G01F 23/20 |
| | | | | 177/126 |
| 4,121,453 A | * | 10/1978 | Levin | A61B 5/1036 |
| | | | | 73/172 |
| 4,219,091 A | * | 8/1980 | Kleinhans | G01G 3/1402 |
| | | | | 177/132 |
| 4,433,741 A | * | 2/1984 | Ryckman, Jr. | G01G 3/1402 |
| | | | | 177/199 |
| 4,744,254 A | | 5/1988 | Barten | |
| 4,765,422 A | * | 8/1988 | Hoffmann | G01G 3/1402 |
| | | | | 177/211 |
| 4,880,069 A | * | 11/1989 | Bradley | G01G 19/44 |
| | | | | 177/211 |
| 4,898,255 A | * | 2/1990 | Gaines | G01G 3/1402 |
| | | | | 177/211 |
| 4,949,799 A | * | 8/1990 | Wernimont | G01G 21/23 |
| | | | | 177/1 |
| 4,993,506 A | | 2/1991 | Angel | |
| 5,086,856 A | * | 2/1992 | Haggstrom | G01G 19/445 |
| | | | | 177/1 |
| 5,276,432 A | * | 1/1994 | Travis | A61B 5/1115 |
| | | | | 177/144 |
| 5,287,757 A | | 2/1994 | Polaert et al. | |
| 5,313,022 A | * | 5/1994 | Piroozmandi | G01L 1/2231 |
| | | | | 177/132 |
| 5,510,581 A | | 4/1996 | Angel | |
| 5,801,339 A | * | 9/1998 | Boult | G01G 17/08 |
| | | | | 177/261 |
| 5,831,221 A | * | 11/1998 | Geringer | G01G 19/445 |
| | | | | 177/144 |
| 5,844,488 A | * | 12/1998 | Musick | G08B 21/22 |
| | | | | 340/286.07 |
| 5,932,848 A | | 8/1999 | Gordon | |
| 6,133,837 A | * | 10/2000 | Riley | G08B 21/22 |
| | | | | 340/524 |
| 6,222,137 B1 | * | 4/2001 | Handford | G01G 19/083 |
| | | | | 177/126 |
| 7,381,910 B1 | * | 6/2008 | Wilkerson | G01G 19/445 |
| | | | | 177/144 |
| 8,664,547 B2 | * | 3/2014 | Werner | G01G 3/10 |
| | | | | 177/211 |
| 9,188,476 B2 | * | 11/2015 | Volker | B01D 61/04 |
| 2002/0023785 A1 | * | 2/2002 | Sternberg | G01G 19/445 |
| | | | | 177/144 |
| 2006/0028350 A1 | * | 2/2006 | Bhai | A61B 5/1115 |
| | | | | 340/666 |
| 2007/0149883 A1 | | 6/2007 | Yesha | |
| 2007/0151357 A1 | | 7/2007 | Kurtz et al. | |
| 2008/0041638 A1 | | 2/2008 | Simons | |
| 2010/0155152 A1 | | 6/2010 | Weichao | |
| 2010/0231376 A1 | * | 9/2010 | Hirose | A61B 5/1115 |
| | | | | 340/517 |
| 2011/0067502 A1 | | 3/2011 | Simons | |
| 2011/0112442 A1 | | 5/2011 | Meger et al. | |
| 2012/0181094 A1 | * | 7/2012 | Gottfriedsen | G01G 23/48 |
| | | | | 177/201 |
| 2012/0182148 A1 | * | 7/2012 | Paine | G08B 21/0461 |
| | | | | 340/573.4 |
| 2015/0173671 A1 | * | 6/2015 | Paalasmaa | A61B 5/0022 |
| | | | | 600/301 |

FOREIGN PATENT DOCUMENTS

| | | |
|---|---|---|
| CN | 101632579 A | 1/2010 |
| CN | 201684102 U | 12/2010 |
| EP | 0301109 A1 | 1/1989 |
| EP | 2 148 179 A1 | 1/2010 |
| GB | 2499602 A | 8/2013 |
| JP | 2962703 B1 | 10/1999 |
| JP | 2006-266894 | 10/2006 |
| WO | 95/31700 | 11/1995 |
| WO | 2007/143838 A1 | 12/2007 |
| WO | 2010/092517 A1 | 8/2010 |

OTHER PUBLICATIONS

Search Report, GB App. 1318201.9, Oct. 27, 2014 (2 pages).

* cited by examiner

WEIGHT SENSOR SUITABLE FOR USE UNDER A BED WITH A DEFORMABLE PLATE MOUNTED TO A BASE AT THREE CONTACT POINTS

TECHNICAL FIELD

The present invention relates to a weight sensor suitable for use under a bed and to a weight sensing system for a bed.

BACKGROUND OF THE INVENTION

A bathroom weighing scale is a commonly used piece of apparatus that allows a user to weigh themself to track their weight. Typically a user will weigh themself at the same time each day, for example when they wake up and enter the bathroom in the morning. Advanced bathroom scales are available that connect, via WiFi, to the internet and allow a user's weight to be remotely logged. The user can then review how their weight has varied over a period of time. However if the user forgets to weigh themself then data is missed and the history of their weight is incomplete.

It is known that a weight sensing unit can be placed under the leg of a bed allowing a component of the weight of the bed plus the weight of the user to be measured. By placing a weight sensing unit under each foot, the total weight of the bed and user can be measured as well as gross changes in weight due to incidents of the user leaving and then returning to bed. Analysis of the variation in the recorded weight will allow determination of the weight of the user by subtracting the weight recorded after the user has left the bed (signified by a large drop in total weight) from the total weight before such an event. In such a manner the user's weight can be reliably logged every day without the user needing to actively switch on and stand on a bathroom weighing scale. An example of such a system can be seen in EP 2148179 A1.

However, a simple weight measuring process using weight sensors positioned under the legs of a bed is only able to give a single weight reading for the whole bed. If two people are using a double bed then changes in weight cannot be distinguished between the two users. Such a system therefore has limitations for multiple bed users.

A weight sensing unit that is to be placed under each foot of a bed will typically consist of a load cell element upon which are mounted one or more strain gauges, a base and a platform, as well as any necessary wires and cables for the strain gauge(s) to be wired e.g., in conventional Wheatstone bridge arrangements. There are a number of typical low profile weight sensors or load cells in the prior art, although not especially designed for use as bed scales. One type is described in U.S. Pat. No. 5,392,848, in which a cantilever load cell is positioned between a base and a platform. However the loads encountered beneath a centre leg of a double bed could rise to 150 kg or more and this type of load cell would need to be excessively thick to accommodate such high loads. A thinner alternative is described in U.S. Pat. No. 5,510,581 and such a design is capable of accommodating high loads without excessive thickness. However such a load cell requires fixing to a platform plate for use as well as requiring a central foot to deliver the central load resulting from its contact with the ground.

U.S. published application 2008/0041638 shows a load cell with a circular load cell comprising a thick circular base with a central contact knob that ensure that a central load is transmitted perpendicular to the load cell either directly or via a platform. Such a load cell may be used for indirect measurement of the weight of objects supported on a platform, such as a pallet or floor. A similar circular load cell is described in U.S. published application 2011/0067502 and again shows a thick circular base and with the option of a central ball bearing to apply the load perpendicular to the load cell via a platform. Finally U.S. published application 2010/0155152 shows a low profile load cell with a central raised bump that again ensures that the central load is transmitted perpendicular to the load cell via contact with a foot element. The base of this load cell does not have a thick section and is designed so that it can rest on a supporting surface without the need for additional fasteners. The same patent application shows an example of a further load cell in the prior art in FIG. 13, again with a central bump and without a thick base.

The various load cells known in the prior art have not been adapted for use in weight sensors intended to bear the weight of bed and be sensitive to changes in weight e.g., when a person moves in their sleep. Moreover it has not previously been possible to independently monitor the weight and weight shifting of two people sharing the same bed.

SUMMARY OF THE INVENTION

According to a first aspect of the present invention there is provided a weight sensor comprising a weighing platform and a load cell coupled to the platform to sense a weight applied to the platform, the load cell comprising a deformable plate with one or more strain gauges arranged to provide an electrical signal representing the weight applied to the platform, and a base supporting the load cell, wherein the deformable plate is movably mounted to the base at only three contact points, the contact points allowing lateral movement of the plate relative to the base when the plate deforms in response to a weight applied to the platform.

It will be appreciated that the deformable plate is movably mounted to the base in a tripod arrangement, which means that it is self-centering when a load is applied off-centre to the platform. This has been found to be particularly beneficial when such a weight sensor is used underneath a bed, as a bed leg or other support member may not be aligned centrally over the weight sensor. The Applicant has recognised that bed legs come in many forms, for example round section, square section, rectangular section, thin, fat, rail and/or with wheels. It is advantageous that a weight sensor according to the present invention is able to cope with these different forms of bed legs as well as misalignment or poor centering of a bed leg relative to the centre of the sensor. Beneficially the sensor is not unduly affected by minor misalignment of the leg of a bed relative to the load cell.

The three contact points between the deformable plate and the base may have any suitable form allowing lateral movement of the plate relative to the base. For example, the contact points may allow the deformable plate to slide relative to the base. The base and/or plate may provide one or more dedicated bearing surfaces for the contact points. In one set of embodiments, the deformable plate may comprise three rounded protrusions arranged to contact a surface of the base, preferably a substantially flat surface. Of course such an arrangement may be reversed, with the base comprising three rounded protrusions to support a lower surface of the deformable plate, preferably a substantially flat surface. In another set of embodiments, the deformable plate may be movably mounted to the base by three ball bearings arranged between the deformable plate and the base. So as to keep the ball bearings positioned at the three contact points, the plate and/or base may comprise three corresponding seats for the three ball bearings.

In order to ensure that the tripod arrangement provides a centering function, preferably the three contact points are equally spaced around the centre of the deformable plate. The deformable plate may have any suitable shape while still taking advantage of the tripod mounting arrangement. However, in a preferred set of embodiments the deformable plate is substantially triangular in plan view and preferably the three contact points are arranged at apices of the triangle. It will be appreciated that a plate may be substantially triangular but comprising truncated corners, which may make it easier to accommodate the triangular plate in a weight sensor having an overall shape that is not triangular e.g. square or round. The deformable plate preferably takes the form of an equilateral triangle (with or without truncated corners). Preferably the three contact points are evenly spaced at the apices of the equilateral triangle. The contact points may take any of the forms already discussed above.

The strain gauge(s) may comprise any suitable strain transducer which undergoes a change in electrical resistance when stretched or compressed. A metal, piezoelectric and/or semiconductor strain gauge may be used. A typical strain gauge may comprise a fine wire or etched foil.

The strain gauge(s) may be formed integrally with the deformable plate or embedded internally. However, it is preferable for the one or more strain gauges to be attached to a surface of the deformable plate, preferably a surface facing the weighing platform. A single strain gauge may be positioned centrally with respect to the deformable plate, but if a load is not applied centrally then this risks an inaccurate reading. It is preferable for multiple sets of strain gauges to be provided, preferably positioned symmetrically about the centre of the deformable plate. Further preferably each set of strain gauges is arranged symmetrically around one of the contacts points. Each set may comprise a single strain gauge or multiple strain gauges, for example a pair of strain gauges. By increasing the number of sets of strain gauges in the plane of the deformable plate, this makes it possible to overcome the effects of lateral and/or eccentric forces.

Furthermore, each set of strain gauges, for example a pair of strain gauges, may be able to cancel out the effects of any lateral loads using a double cantilever arrangement. Thus in one set of embodiments each set of strain gauges comprises a pair of flexure beams that are arranged to bend into symmetrical double cantilever S-shapes in the plane of the deformable plate. With one of the pair of strain gauges compressing and the other stretching symmetrically, the effect of any lateral loads can be effectively cancelled out.

In embodiments where the deformable plate has a triangular form, three sets of strain gauges may be aligned with the three apices of the triangle. Preferably each set of strain gauges is arranged in alignment with one of the contacts points. The strain gauges may therefore share the same tripod arrangement as the deformable plate.

One or more alternative, or additional, ways of ensuring an even load distribution may be included in the load cell design. In one set of embodiments the platform and deformable plate are coupled by a single central coupling, preferably positioned centrally with respect to the deformable plate. This ensures that even if a load, for example transmitted by a bed leg, is applied to the platform off-centre then it is still applied centrally to the deformable plate. The load can then be spread by the deformable plate to the strain gauge(s), preferably multiple strain gauges arranged symmetrically around the central coupling. The central coupling may, for example, comprise a rounded protrusion extending from a surface of the plate towards a facing surface of the platform or vice versa. Such a rounded protrusion can allow the platform to tip from side to side while still transmitting a load axially into the deformable plate. Accordingly the sensor may not be unduly affected by minor misalignment of the load, e.g. applied by a bed leg, relative to the middle of the sensor.

It has been recognised that there may sometimes be gross misalignment between the weight applied to the platform and the centre of the load cell, for example if a bed leg were to be positioned almost hanging off the platform. In such situations the weight sensor may not be able to accurately detect the load e.g. from a bed and it would be advantageous to have a warning system so that a user is alerted to the problem. Thus in a set of embodiments the sensor may further comprise means for sensing when a periphery of the deformable plate is moved in contact with the base. Alternatively, or in addition, a sensing means may be arranged to detect when the deformable plate loses contact with the base at one of the three contact points. Such sensing means therefore detects when the deformable plate is not stably mounted to the base in a tripod arrangement but tilted over to one side. The sensing means may be electrically attached to an alarm, for example a visual and/or audible alarm, to alert a user to the misalignment. Such sensing means may comprise, for example, a pair of peripheral contacts on the facing surfaces of the deformable plate and the base. The sensing means may detect when the platform has tilted far enough to touch the load cell or the base.

The weight sensor may detect when it is being tipped, for example due to misalignment of a bed leg hanging over the edge, using a motion sensor or proximity switch e.g. a microswitch. As with the internal sensing means, this may trigger an alarm to alert a user.

The weighing platform should be designed to be strong enough to bear the typical weight transmitted by a bed leg or other bed support, for example up to 150 kg for the centre leg of a double bed. Preferably the weighing platform comprises a substantially flat upper surface on which the bed leg or other support member can rest. As beds are subject to their user's lateral movements, it is preferable for the platform to be able to resist relative movement of the bed relative to the sensor. Accordingly the weighing platform may comprise an upper surface or cover made of a resilient or gripping material, for example silicone rubber.

In addition, or alternatively, the weighing platform may include one or more feature to assist in alignment of a bed leg or other support member. In one set of embodiments, the platform may include a recess positioned centrally on its upper surface. Such a recess may provide a location point for a wheel or castor affixed to the bottom of a bed leg. Whether or not a recess is provided, the platform may include a central pad to help with alignment of a bed leg over the centre of the sensor. By providing such a recess and/or pad on the weighing platform misalignment can be avoided.

A weight sensor as disclosed above may be used in a range of situations. However, one particularly preferred application is for weighing the load, and changes in load, of a bed as it used by one or more people. In other words, a weight sensor may be used to measure the absolute weight of one or more occupants of a bed, and changes in weight with time. It is therefore desirable for the sensor to be an unobtrusive as possible, so that it can be placed under each leg, foot, rail or other support member of a bed. It is preferable for the weight sensor to be relatively thin or low in profile. It desirable for the weight sensor to have a size and shape that makes it universal for use with beds having different support members. It is therefore preferable for the weight sensor to comprise a generally planar weighing platform, e.g., rather than a cup-shaped platform that can only be used with legs and not rails. In preferred embodiments the weight sensor may take the form of a generally flat pad, i.e., that is much thinner than it is wide. The weight sensor may have any suitable shape, including square, rectangular, polygonal, etc. but a round shape may be preferred so as to avoid any sharp corners that may cause harm to a user. In order for the weight sensor to resist ingress of dust and dirt, it is preferable for the platform to be sealed to the base. In embodiments where the platform comprises a resilient cover then this can conveniently be attached to the base to also provide a seal.

The weight sensor may of course include any necessary wires/cables for the strain gauge(s), especially where multiple strain gauges are wired in Wheatstone bridge arrangements. The strain gauge(s) may be electrically connected to local and/or remote data collection means. The weight sensor may include a memory that can store load data generated by the strain gauge(s), at least temporarily. However it is preferable for weight data sensed by the strain gauge(s) to be transferred elsewhere so that the sensor itself does not need space to accommodate a memory. A preferred system for monitoring loads, for example from a bed, includes multiple weight sensors electrically connected to a shared data hub. The data hub is preferably arranged to continuously collect load data from the weight sensors during use. Such a system may therefore monitor how the absolute weight of a bed and its occupant(s) changes in time, for example for long term assessment. The data hub may comprise a memory arranged to store load data received from each of the weight sensors.

The memory in the data hub may store the raw electrical signals e.g. in digital format. In order to potentially reduce the memory size required, the hub may further comprise a processor arranged to process electrical signals generated by the strain gauge(s) and record load data for storage. As is mentioned above, the data hub is preferably arranged to continuously, rather than periodically, collect load data during use. This can be important where the sensors are used not only to detect the absolute weight of a user but also patterns of weight shifting, for example while sleeping. However, such continuous monitoring could generate a large amount of data that could quickly fill up the memory if it were all stored. The Applicant has recognised that during many periods of time, e.g. during the day or during restful sleep, the load data from a bed may be substantially constant. It may only be useful to collect load data during times when there are changes in load. Thus in a preferred set of embodiments the data hub comprises a processor arranged to record load data relating to a change of load. Furthermore the memory may be arranged to store only the recorded load data e.g. only load data relating to a change of load. Other load data may be discarded after having been collected. This reduced the burden on the memory and any wireless data connection.

The load data, whether raw or processed, may be stored in a removable memory device, such as a SD memory card, that a user can take out of the hub. Alternatively, or in addition, the data hub may comprise data connection means for the memory, such as a USB port. An advantage of the hub comprising a local memory is that it does not require a permanent connection to an external server, in particular a wired connection may be avoided.

Alternatively, or in addition, the data hub may comprise wireless data connection means, for example a wireless transceiver. The hub may be configured to transfer load data using any suitable wireless communication protocol, such as WiFi or Bluetooth. Preferably the wireless data connection means is arranged to transfer only recorded load data, e.g. load data relating to a change in load. Such a wireless connection can enable the hub to transmit load data continuously or periodically to an external server. Data collected by the external server can be made available over the Internet, for example displayed to a user via a website or smart phone app.

A data hub electrically connected to multiple weight sensors may advantageously be used to collect weight data from a bed. Accordingly, the system may comprise the plurality of weight sensors positioned on the ground under a free-standing bed to monitor loads from the bed, for example with a weight sensor positioned under each of the four corners of the bed, or several sensors positioned under a side rail, and possibly another weight sensor positioned under a central leg or support member. A free-standing bed is one which is not connected to a wall but transmits all of its load to the ground. Such a weight sensing system may be used to monitor the daily weight of a person using the bed and/or weight changes providing active information such as respiratory rate or heart rate e.g. ballistocardiography (BCG). Furthermore, the Applicant has realised that by recording load changes it is possible to detect when one or more people get into or out of the same bed and hence independently measure the absolute weight of multiple occupants.

However a system that simply the sums or averages the load data collected from multiple weight sensors cannot be used to distinguish load change patterns for two people sharing the same bed, for example for sleep monitoring purposes. If there is a change in load distribution while a bed has multiple occupants then the system cannot determine which occupant has moved. It has been recognised that an improved system comprises a first set of weight sensors arranged under a first side of a bed, and a second set of weight sensors arranged under a second side of a bed, wherein the data hub records a differential measurement of the loads between the first and second sets of weight sensors. Such a differential measurement can be used to separate the load signals from different sides of the bed.

This is considered novel and inventive in its own right, and thus when viewed from a further aspect the present invention provides a weight sensing system for a bed having more than one occupant, the system comprising: a first set of weight sensors arranged under a first side of a bed, a second set of weight sensors arranged under a second side of a bed, and a circuit connecting the weight sensors that is arranged to measure a difference between the weight(s) sensed by the first and second sets of weight sensors.

It will be appreciated that in such a system the sensors are not wired up to give a single absolute weight reading, but wired up to give the difference between the sensors on the left and right sides of a bed. This difference measures a shift of weight from one side of the bed to the other, or more importantly motion/disturbance/vibration which is off-centre. For example, a person on one side of a shared bed, moving in their sleep, will perturb the signal in one direction and movement of a person on the other side of the bed will perturb the signal in the opposite direction. This can be used to express the weight information from two people on different sides of a bed in a single signal with two poles.

The circuit connecting the weight sensors may comprise a data hub as described above. The data hub may be arranged to record differential weight data, e.g. using a processor.

Preferably the system is arranged to continuously collect weight data from the first and second sets of weight sensors. The differential weight data may therefore be used to track fluctuations in weight and provide reports on breathing and heart rate, sleep quality, sexual activity, etc. In addition, the data hub may also be arranged to record absolute weight data, especially relating to a change of weight. The system can therefore monitor the absolute weight of multiple occupants in the same bed and use weight changes, e.g. when one person enters or leaves the bed, to distinguish the two independent weights.

The data hub may comprise a memory. To minimise the amount of weight data to be stored, the memory is preferably arranged to store only the record weight data. In addition, or alternatively, the system preferably further comprises a wireless data connection so that recorded weight data can be transferred to an external server. While the data hub may provide some local processing, preferably the differential weight data is further processed at the external server.

BRIEF DESCRIPTION OF THE DRAWINGS

Some preferred embodiments of the present invention will now be described, by way of example only, and with reference to the accompanying drawings, in which.

DETAILED DESCRIPTION

Figure 1:
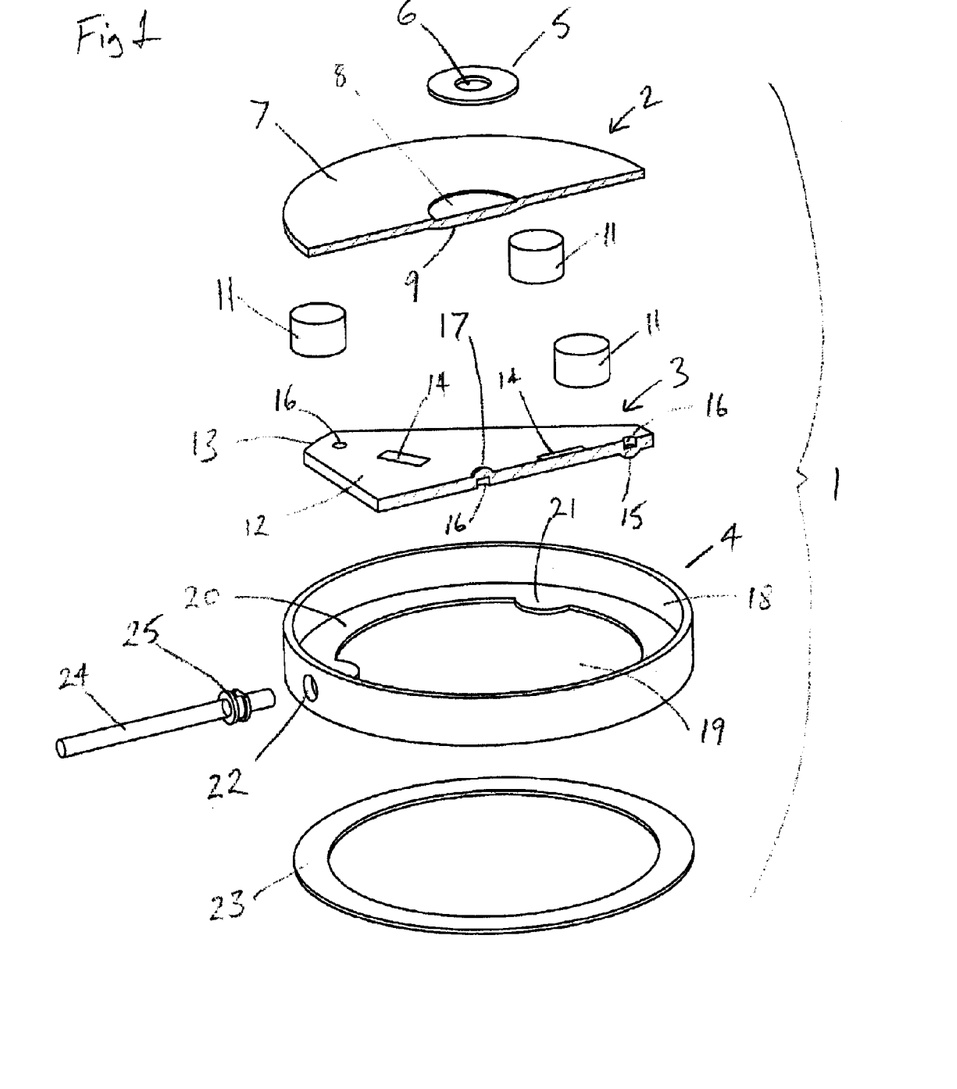
FIG. 1 is an exploded perspective view of a first embodiment of a sensor pad, with the platform and load cell shown as half sections.

Referring to FIG. 1 there is shown an exploded perspective view of a sensor pad 1 consisting of an upper platform 2 mounted over a load cell 3 and a base 4. The base 4 has a bottom 19, side wall 18, an optional bearing surface 20 with optional mounting pads 21 and a cable cut-out 22. An optionally truncated triangular plate 12 (shown as a half section) with an apex bump 15 at each of three apexes 13 on a bottom surface of the plate 12, one or more strain gauges 14 mounted to either the top, bottom or both surfaces of plate 12, a central bump 17 on a top surface of the plate 12 and optional bump recesses 16 to aid the formation of the bumps 15, 17, can be placed into the base 4 so that the three apex bumps 15 rest on the bearing surface 20, or optionally directly on the bottom 19, such that the load cell 3 sits in a stable manner by virtue of having three points of contact.

The platform 2 consists of a top disc 7 with an optional upper recess 8, and an optional thickened section 9 can be placed on top of load cell 3 so that platform 2 rests on central bump 17. Any vertical force due to a load resting generally centrally on platform 2 will therefore be transmitted through the central bump 17 and then equally distributed via each of the three apex bumps 15 to the base 4. If base 4 is placed onto the floor and the leg of a bed is placed centrally on top of platform 2, the vertical force due to a component of the weight of the bed (and any occupant) will be transmitted through load cell 3 causing it to deform. The deformation can be detected using one or more strain gauges 14 forming an arm/arms of a Wheatstone bridge, a standard way to detect deformation in load cells.

An optional resilient bottom pad 23 can be placed between base 4 and the ground and an optional resilient top pad 5 can be placed between platform 2 and a bed leg (not shown). A pad recess 6 in top pad 5 is provided so that if a wheel is attached to the leg of a bed, the wheel can be stabilised by being placed into the pad recess 5. A cable 24 and cable relief bush 25 allow excitation and sense wires for the strain gauge/gauges to enter the pad 1 and resilient adhesive pads 11 (or any other connection means such as Velcro or magnets) can be positioned between platform 2 and base 4 of the load cell 3 so that the pad 1 does not come apart when handled. Whilst apex bumps 15 and central bump 17 are shown as rounded domes, the important requirement is that they have point contact and are able to slide relative to the surfaces they touch. In this manner any minor lateral motion due to a bed leg flexing sideways or any spreading of the apex bumps 15 due to deformation of the load cell 3 does not result in complex lateral deformation of the load cell 3. Only vertical motion can be stored in the load cell 3 as it deforms.

Figure 2:
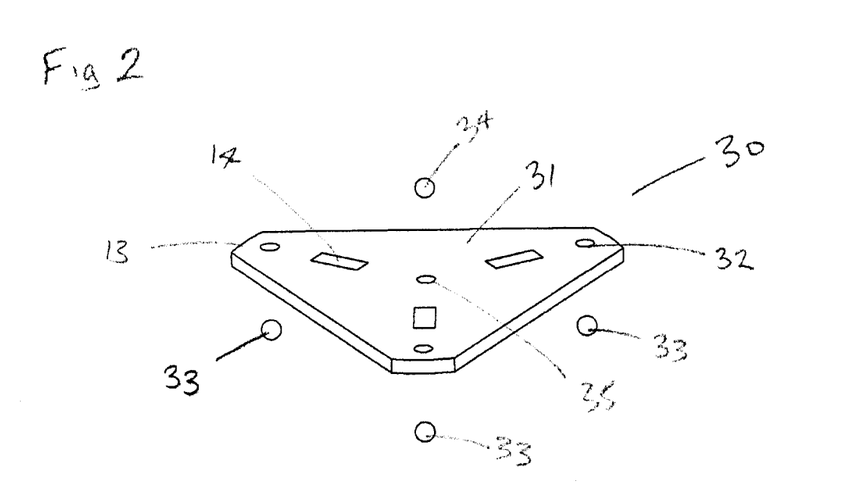
FIG. 2 is a perspective view of an alternative load cell.

FIG. 2 shows an alternative construction for an optionally truncated triangular ball load cell 30 in which a simple plate 31 with holes has apex holes 32 at each of its apexes 13 and corresponding apex balls 33 that are too large to pass through, and a central hole 35 with a corresponding central ball 34 that is too large to pass through. The balls 33, 34 may be steel ball bearings. The advantage of this alternative construction is that the ball load cell 30 is simpler to manufacture and the flat profile makes the fitting of strain gauges 14 simpler on a production line. The balls in FIG. 2 act in the same manner as the bumps in FIG. 1, ensuring that any vertical force passes from the platform 2, via the central ball 34, through the deformed plate 31 with holes and equally through the three apex balls 33 into the base 4. Any lateral force does not lead to deformation as the balls 33, 34 are free to slide on their contact surfaces with the base 4 and platform 2.

Figure 3:
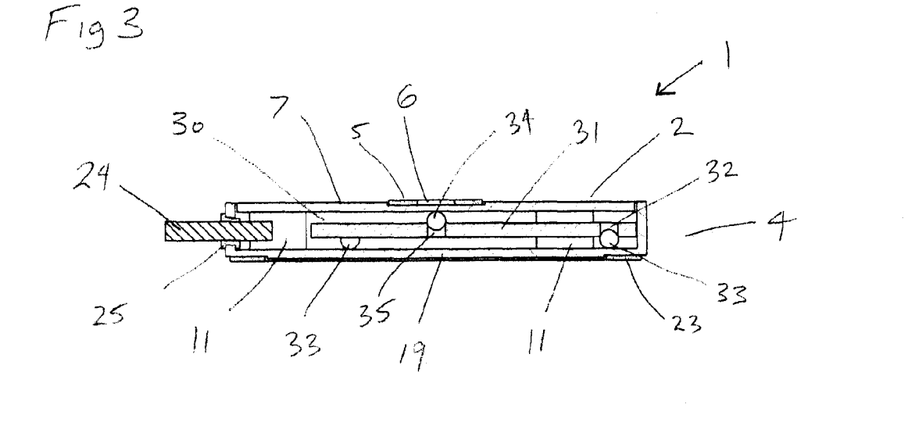
FIG. 3 is a half section of a pad fitted with the load cell of FIG. 2.

FIG. 3 shows a pad 1 fitted with a ball load cell 30 and the apex balls 33 can be seen resting on bottom 19 of base 4 which is shown without bearing surface 20. Top disc 7, which is shown without thickened section 9, of platform 2 can also be seen resting on central ball 34.

Figure 4:
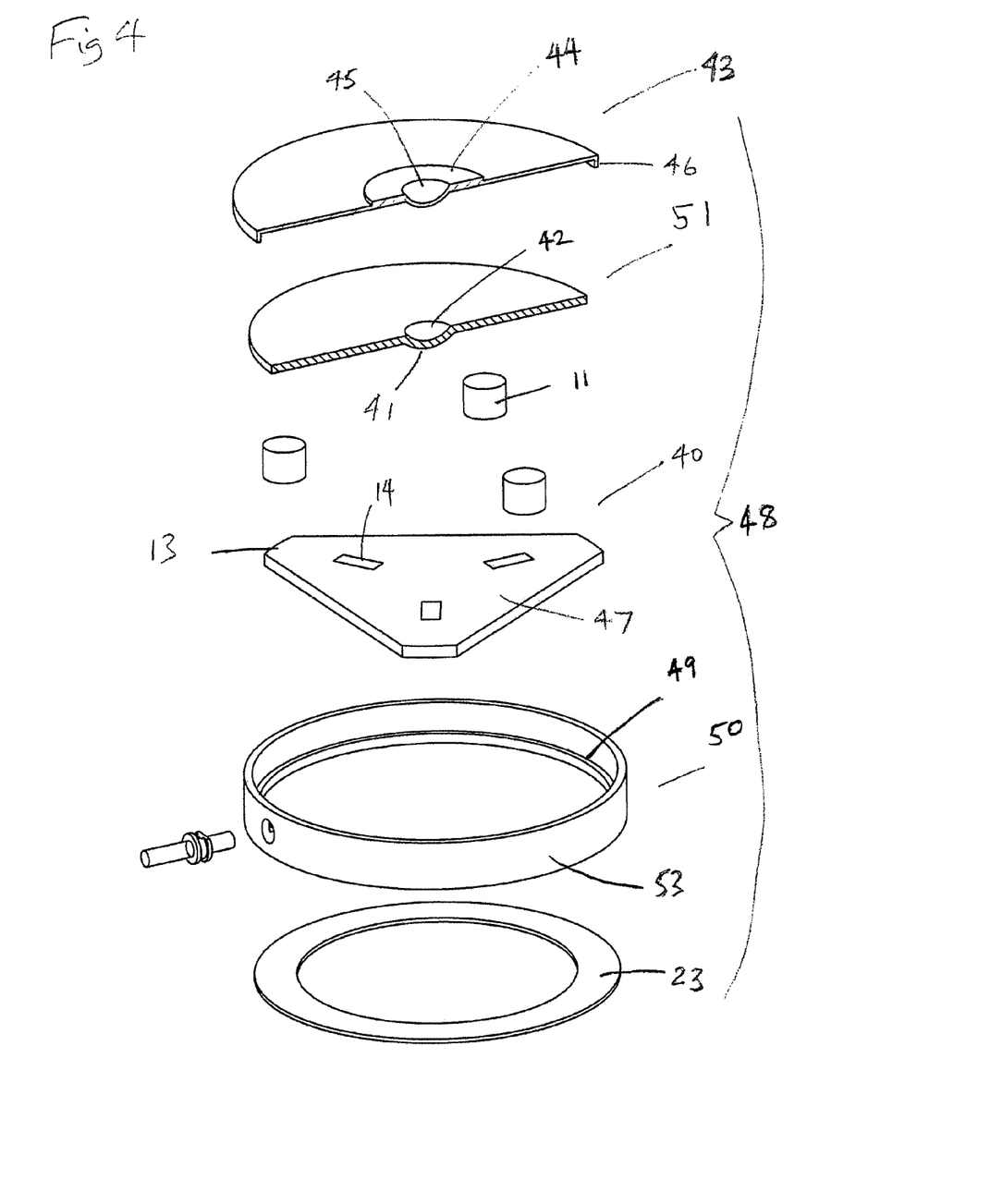
FIG. 4 is an exploded perspective view of another embodiment of a sensor pad with a plain load cell, with the platform and platform cover shown as half sections.

FIG. 4 shows another embodiment in which a plain sensor pad 48 contains an optionally truncated triangular plain load cell 40 consisting of a plain plate 47 mounted with one or more strain gauges 14. The plain load cell 40 does not require any balls and holes or integrated bumps as it simply rests on a support surface 49 within plain base 50. A plain platform 51 has a central platform bump 41 on a bottom surface that rests against the centre of plain plate 47 and transmits any force acting on the plain platform 51 into plain load cell 40 which will deform due to the stable support provided at each plain plate apex 52 by support surface 49. An optional central platform recess 42 provides a location point for a wheel that may be affixed to the bottom of a bed leg (not shown) and a resilient top cover 43 may be placed to cover the plain platform 51 and provide an optional top cover recess 45 to match the central platform recess 42 and a top cover pad 44 to help align more conventional bed legs to the centre of the plain pad 48. A top cover return 46 is provided to wrap around plain base side wall 53 and seal plain pad 48 against dirt ingress. By using a thin and flexible material such as silicone rubber for top cover 43, the resistance to deformation will have a negligible effect on the deformation of the load cell.

Note that strain gauge wiring is not shown in FIGS. 1 to 4.

Figure 5:
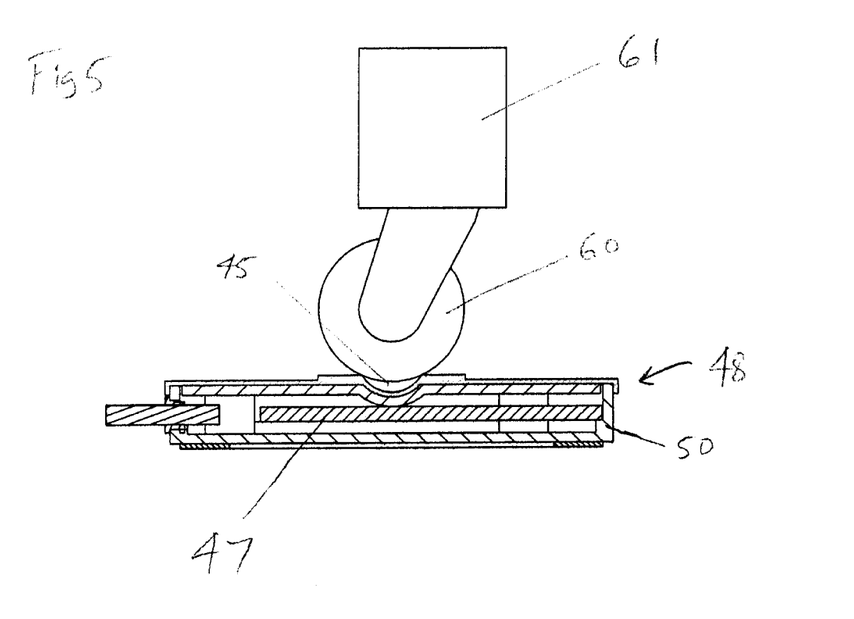
FIG. 5 is a half section of the sensor pad of FIG. 4 showing a bed leg with an attached wheel resting on the pad.

FIG. 5 shows a bed leg 61 with a leg wheel 60 resting in top cover recess 45 of plain pad 48 to keep it centrally located.

Figure 6:
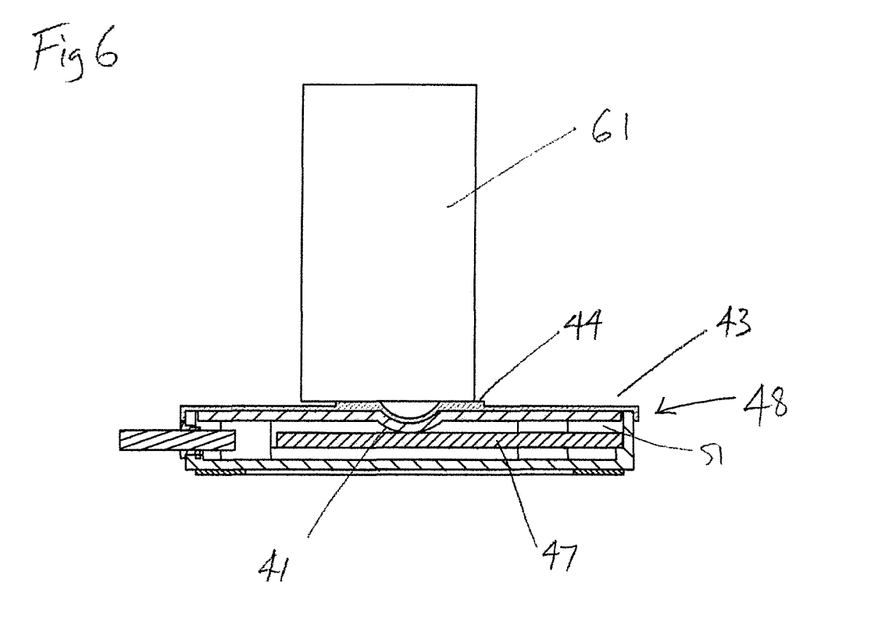
FIG. 6 is a half section of the sensor pad of FIG. 4 showing a slightly misaligned bed leg sitting on the pad.

FIG. 6 shows a bed leg 61 resting on top cover pad 44 of resilient top cover 43. Even though the bed leg 61 is misaligned, the vertical force acting through it will be transferred vertically into plain plate 47 due to the point contact of the domed face of central platform bump 41. Tipping of platform 51 is avoided due to the area of contact between top cover pad 44 and bed leg 61.

Figure 7:
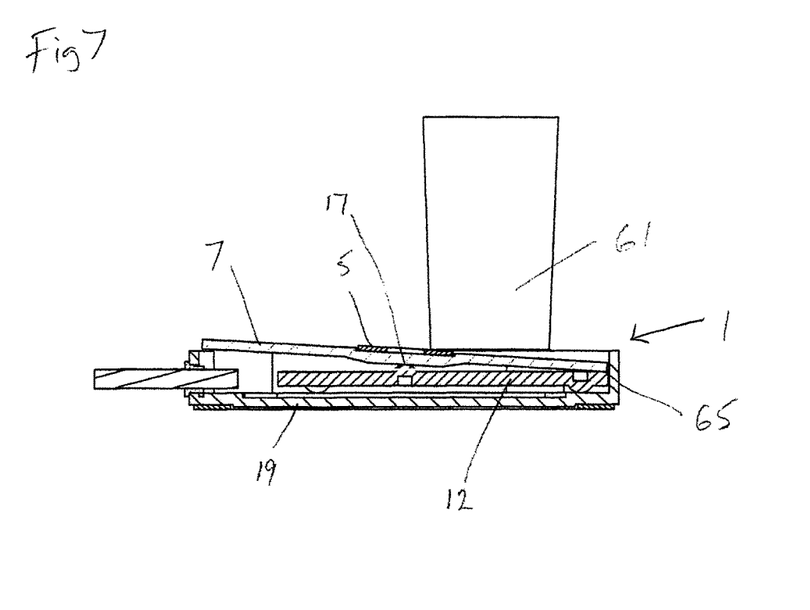
FIG. 7 shows a half section of the sensor pad of FIG. 1 with a grossly misaligned bed leg causing the platform to tilt until it touches the load cell.

FIG. 7 shows the sensor pad 1 of FIG. 1 with a grossly misaligned bed leg 61 resting on top pad 5 such that it causes top disc 7 to pivot on central bump 17 until it comes into contact with load cell 3 at contact point 65. Under such a condition the vertical load being transmitted by bed leg 61 is no longer passing only through the central bump 17. This will result in load cell 3 not deforming sufficiently and an incorrect measurement of the weight carried by the bed leg being derived from the strain gauges. By attaching peripheral contacts to each of the top disc 7 and the load cell 3, it is possible to detect such contact occurring when the sensing wires touch each other and are connected to a circuit that can alert the user or log a fault condition. If the top disc 7 and load cell 3 are constructed from a conductive material such as aluminium or steel, an insulator (not shown) may be placed between them at the central bump 17 and sensor wires attached to each component so that unwanted contact can be detected and the user alerted without the need for peripheral contacts. Contact detection can also be arranged so that contact is detected between the platform and the base or the platform and a dedicated contact ring.

It will be seen that the different arrangement of load cells and pads have a common theme of a triangular load cell that is supported at its three apexes (which may be truncated) and centrally loaded via a domed contact point. In this way the load acting through the platform is transferred into the load cell causing it to deform. The central domed contact point ensures that the vertical component of any force acting on the platform is the dominant force transmitted to the load cell with lateral forces being negligible.

As the load cell deforms due to the vertical load, strain gauges on the top surface of the plate will be compressed and strain gauges on the bottom surface of the plate will be stretched. By connecting one or more strain gauges to the cable and/or to each other to provide well established arrangements such as quarter, half or full Wheatstone bridges, a change in deformation can be converted to a change in resistance and voltage across the Wheatstone bridge which can be calibrated to correspond to the load being applied to the pad. For a full bridge arrangement two pairs of opposed strain gauges would be connected to each other and then to a pair of sensing wires and a pair of excitation wires, as commonly found in the field of load cells.

Figure 8:
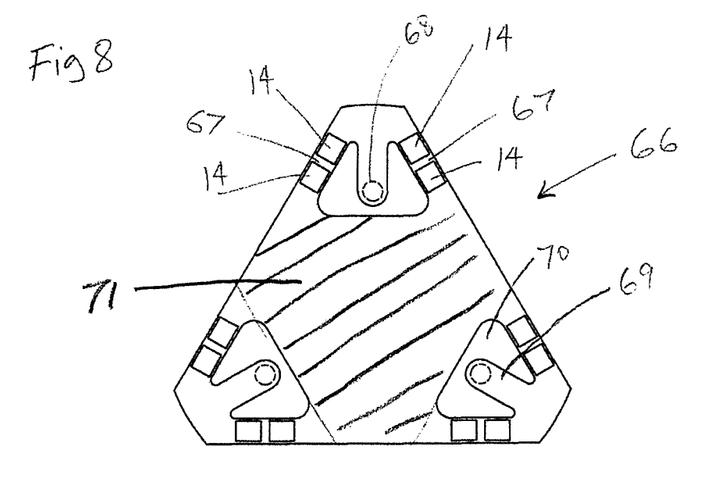
FIG. 8 shows a plan view of a six beam load cell that may be used in a modified sensor pad.
Figure 9:
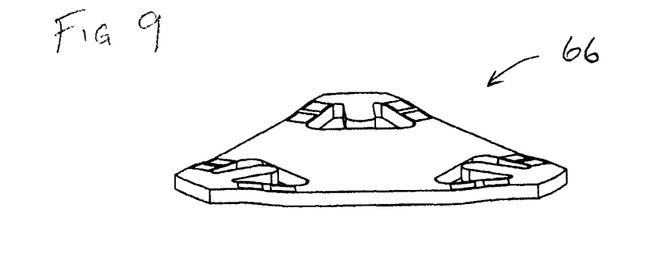
FIG. 9 shows the six beam load cell of FIG. 8 when it is under load.

FIG. 8 shows a further embodiment in which a six beam load cell 66 that has six beams 67 each mounted with a pair of strain gauges 14. Three beam bumps 68 on the underside of the six beam plate 71 are mounted on three tongues 69 arranged so that if a load is placed anywhere between the three beam bumps 68 each pair of beams 67 will bend in an 's' shaped fashion as shown in FIG. 9 so that on each beam there will be one strain gauge 14 in compression and one in tension. The strain gauges 14 can be wired together in a conventional manner to allow the two pairs of strain gauges 14 at each apex to act in Wheatstone bridges and allow the deformation of the beams 67 to be converted into a measure of the force being applied. In this case the strain gauges 14 can be connected so that each pair of beams 67 acts as an independent load cell and the total load measured by the three load cells is equal to the load acting through the bed leg. For this reason a central bump is not required to ensure that equal loads passes through each beam bump. Instead the platform can be connected to the central area 71 of the six beam load cell (shown with hatched lines) by adhesive or other means.

A weight sensor as described hereinabove, or other variants within the scope of the present invention, may be used in a weight sensing system for a bed having one or more occupants. Such a system may comprise multiple weight sensors, for example distributed equally underneath a bed. In one example, such a system has been deployed to monitor weight changes for a bed having two occupants. From FIG. 10 it can be seen that a weight measurement graph can be generated from recording changes to the weight signal e.g. when someone gets into or out of the bed. By recording the changes in weight, the system is effectively self-zeroing and can eliminate effects e.g. due to changing the bed sheets. Furthermore, by only recording and storing changes in the weight signal, the system can keep the amount of stored data to a minimum even if the weight sensor(s) collect a weight reading every second.

Figure 10:
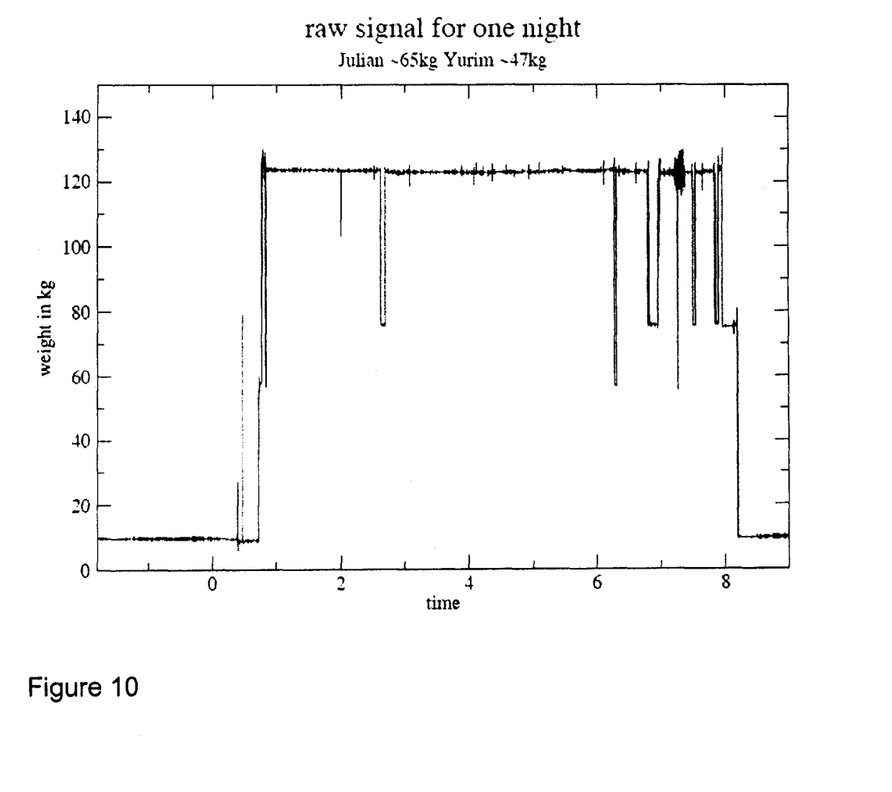
FIG. 10 shows the absolute weight data and changes sensed for a bed over one night.
Figure 11:
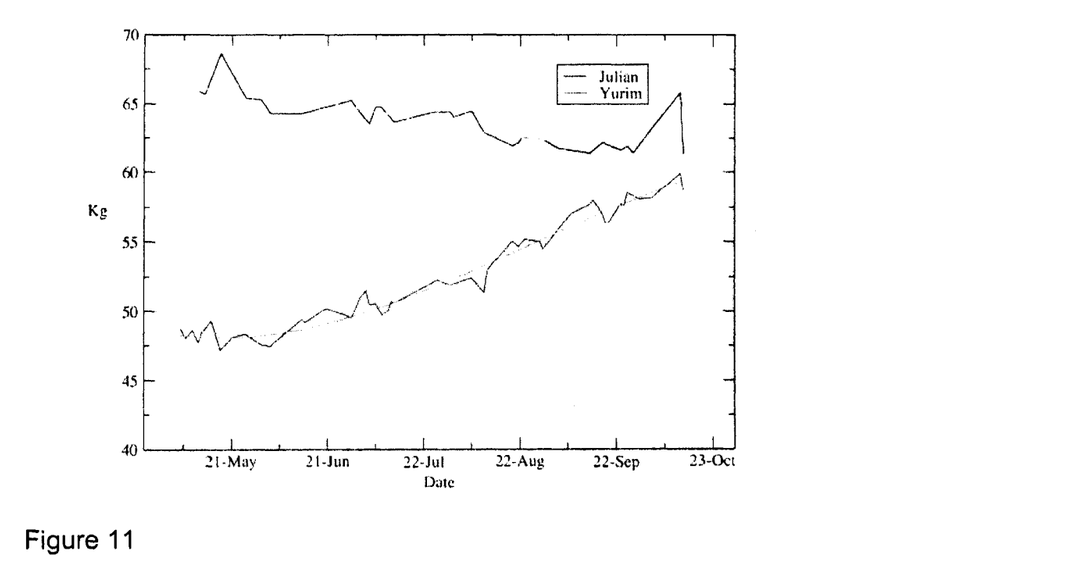
FIG. 11 shows the daily weight recorded for two occupants of the same bed over a period of five months.

From FIG. 10 it can be seen how the weight changes when one occupant leaves the bed for a short time. In the morning there is a weight change reduction when one person gets up, then the second person is seen to stay in bed for a further period of time. The system is therefore able to separate the absolute weight signals from the two occupants. FIG. 11 shows the absolute weights measured for a husband and pregnant wife sharing the same bed for five months during the pregnancy.

Figure 12:
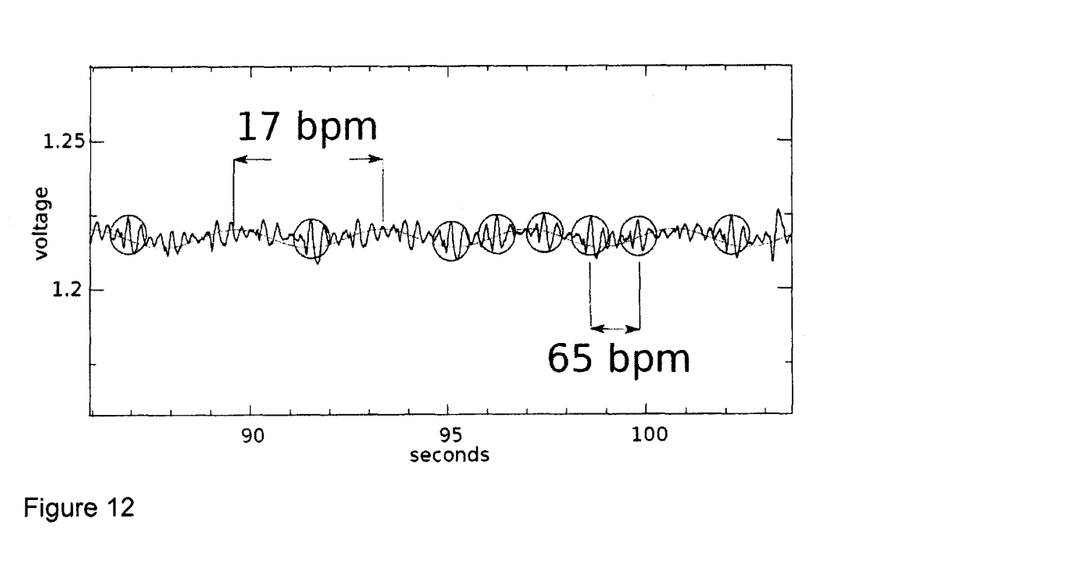
FIG. 12 shows ballistocardiography measurements from weight sensors under a bed.

Finally, FIG. 12 shows how small changes in weight measured by a bed monitoring system can be used to monitor breathing and heart rate.

We claim:

1. A weight sensor, comprising: a weighing platform and a load cell coupled to the platform to sense a weight applied to the platform, the load cell comprising a deformable plate with one or more strain gauges arranged to provide an electrical signal representing the weight applied to the platform, and a base supporting the load cell, wherein the deformable plate is movably mounted to the base at only three contact points, the contact points allowing lateral movement of the plate relative to the base when the plate deforms in response to a weight applied to the platform.

2. A weight sensor according to claim 1, wherein the deformable plate is substantially triangular in plan view.

3. A weight sensor according to claim 2, wherein the three contact points are arranged at apices of the triangle.

4. A weight sensor according to claim 1, wherein multiple sets of strain gauges are positioned symmetrically about the centre of the deformable plate.

5. A weight sensor according to claim 4, wherein each one of three sets of strain gauges is arranged symmetrically around one of the three contacts points.

6. A weight sensor according to claim 4, wherein each set of strain gauges comprises a pair of flexure beams that are arranged to bend into symmetrical double cantilever S-shapes in the plane of the deformable plate.

7. A weight sensor according to claim 1, wherein the platform and deformable plate are coupled by a single central coupling.

8. A weight sensor according to claim 7, wherein the central coupling comprises a rounded protrusion extending from a surface of the plate towards a facing surface of the platform.

9. A weight sensor according to claim 1, wherein the deformable plate comprises three rounded protrusions arranged to contact a surface of the base as the three contact points.

10. A weight sensor according to claim 1, wherein the deformable plate is movably mounted to the base by three ball bearings arranged between the deformable plate and the base as the three contact points.

11. A weight sensor according to claim 1, further comprising means for sensing when a periphery of the deformable plate is moved in contact with the base.

12. A weight sensor according to claim 11, wherein the sensing means comprises a pair of peripheral contacts on facing surfaces of the deformable plate and the base.

13. A weight sensor according to claim 1, wherein the platform comprises an upper surface or cover made of a resilient or gripping material.

14. A weight sensor according to claim 1, wherein the platform includes a recess positioned centrally on its upper surface.

15. A system for monitoring loads, comprising a plurality of the weight sensors according to claim 1 and a data hub electrically connected to each of the weight sensors.

16. A system according to claim 15, wherein the data hub is arranged to continuously collect load data from the weight sensors during use.

17. A system according to claim 15, wherein the data hub comprises a processor arranged to record load data relating to a change in load.

18. A system according to claim 17, wherein the data hub comprises a memory arranged to store only the recorded load data.

19. A system according to claim 15, wherein the data hub comprises wireless data connection means.

20. A system according to claim 15, wherein the weight sensors are positioned on the ground under a free-standing bed to monitor loads from the bed.

21. A system according to claim 15, comprising a first set of weight sensors arranged under a first side of a bed, and a second set of weight sensors arranged under a second side of a bed, wherein the data hub is arranged to record a differential measurement of the loads between the first and second sets of weight sensors.

* * * * *